US012797111B2

(12) United States Patent
Ott et al.

(10) Patent No.: US 12,797,111 B2
(45) Date of Patent: Nov. 17, 2026

(54) HEMOSTATIC DEVICE

(71) Applicant: MATRIA HEALTH TECHNOLOGIES, Saint Martin D'Heres (FR)

(72) Inventors: Franck Ott, Saint Jean de Bournay (FR); Ethel Cappelletti, Voiron (FR); Pascal Barrier, Annecy (FR)

(73) Assignee: MATRIA HEALTH TECHNOLOGIES, Saint Martin D'Heres (FR)

( * ) Notice: Subject to any disclaimer, the term of this patent is extended or adjusted under 35 U.S.C. 154(b) by 70 days.

(21) Appl. No.: 18/842,897

(22) PCT Filed: Mar. 7, 2023

(86) PCT No.: PCT/EP2023/055803
§ 371 (c)(1),
(2) Date: Aug. 30, 2024

(87) PCT Pub. No.: WO2023/170101
PCT Pub. Date: Sep. 14, 2023

(65) Prior Publication Data

US 2025/0195107 A1 Jun. 19, 2025

(30) Foreign Application Priority Data

Mar. 9, 2022 (EP) .................................... 22305266

(51) Int. Cl.
*A61B 17/42* (2006.01)
*A61B 17/00* (2006.01)
*A61B 90/00* (2016.01)

(52) U.S. Cl.
CPC .............. *A61B 17/42* (2013.01); *A61B 90/03* (2016.02); *A61B 2017/00477* (2013.01);
(Continued)

(58) Field of Classification Search
CPC ......... A61B 17/42; A61B 90/03; A61B 90/37; A61B 2090/034; A61B 2017/00477;
(Continued)

(56) References Cited

U.S. PATENT DOCUMENTS

2005/0240074 A1* 10/2005 Lubock ................ A61N 5/1015
600/3
2013/0165969 A1 6/2013 Blin
(Continued)

FOREIGN PATENT DOCUMENTS

CN 111248965 1/2021
CN 214907600 11/2021
(Continued)

OTHER PUBLICATIONS

PCT Search Report in related PCT Application No. PCT/EP2023/055803, Mailed May 10, 1023.
(Continued)

*Primary Examiner* — Shaun L David
*Assistant Examiner* — Cherie M Poland
(74) *Attorney, Agent, or Firm* — Thomas Horstemeyer LLP.

(57) ABSTRACT

The disclosure relates to a hemostatic device comprising a hollow shaft comprising an inner channel configured to be fluidically connected to a vacuum source, hollow ribs fixed to the shaft where each rib comprises an inner channel to be fluidically connected to the shaft and holes leading to the inner channel of the respective rib, a membrane configured to be placed to face a bleeding area of a cavity, holes being arranged to face the bleeding area to induce a negative pressure in the cavity when a vacuum source is applied, the induced negative pressure being configured to attract to the ribs, and a mechanism configured to allow the insertion and extraction of the hemostatic device into the cavity and an
(Continued)

expanded position, and wherein the membrane and the ribs fit the cavity.

15 Claims, 6 Drawing Sheets

(52) U.S. Cl.
CPC ............... *A61B 2017/00566* (2013.01); *A61B 2017/00862* (2013.01); *A61B 2090/034* (2016.02)

(58) Field of Classification Search
CPC A61B 2017/00566; A61B 2017/00862; A61B 2017/12004; A61B 2017/306; A61B 2017/4216; A61B 18/1492; A61B 18/1206; A61B 18/00577; A61B 2050/006; A61B 2017/2948; A61M 25/0017; A61M 25/005; A61M 25/007; A61M 25/04; A61M 25/008; A61M 27/008; A61M 1/84; A61M 1/73; A61M 1/90; A61M 2230/30; A61M 2230/40; A61M 2230/06; A61M 2010/1085; A61M 2010/1089; A61K 31/341
See application file for complete search history.

(56) References Cited

U.S. PATENT DOCUMENTS

| | | | | |
|---|---|---|---|---|
| 2017/0281231 | A1* | 10/2017 | Broderick et al. . | A61B 17/4241 |
| 2018/0161485 | A1 | 6/2018 | Blin | |
| 2020/0246069 | A1* | 8/2020 | Rioux ................ | A61B 18/1492 |
| 2020/0352602 | A1 | 11/2020 | Norred | |
| 2021/0068865 | A1* | 3/2021 | Balasubramaniam ....................... | A61B 17/3431 |
| 2021/0370019 | A1* | 12/2021 | Erbey, II ........... | A61M 25/0017 |
| 2022/0354507 | A1* | 11/2022 | Ott .......................... | A61M 1/90 |
| 2025/0177003 | A1* | 6/2025 | Urvoy .................... | A61B 17/42 |

FOREIGN PATENT DOCUMENTS

| | | | |
|---|---|---|---|
| EP | 3248624 | A1 | 11/2017 |
| SU | 1431746 | A1 | 10/1988 |
| WO | 2020123525 | A1 | 6/2020 |

OTHER PUBLICATIONS

European Search Report in related EP Application No. 22305266.3, mailed Aug. 30, 2022.

* cited by examiner

HEMOSTATIC DEVICE

CROSS REFERENCE TO RELATED APPLICATIONS

This application is the 35 U.S.C. § 371 national stage application of PCT Application No. PCT/EP2023/055803, filed Mar. 7, 2023, which application claims the benefit of European Application No. EP 22305266.3 filed Mar. 9, 2022, both of which are hereby incorporated by reference herein in their entireties.

TECHNICAL FIELD

The present disclosure relates to a hemostatic device, in particular intended to stop or reduce hemorrhages in a natural body cavity such as a uterus.

TECHNICAL BACKGROUND

After childbirth, the mother's uterus is generally subjected to contractions that allow to stop the bleeding caused by the detachment of the placenta.

However, in some cases, the uterus may suffer from atony, so that such contractions do not occur or are not sufficient to stop the bleeding, thereby generating a risk of maternal hemorrhage.

Various hemostatic devices have been developed to promote the contraction of the uterus and help stopping or reducing the hemorrhage.

Document EP 3 248 624 teaches a hemostatic device for treating postpartum hemorrhage, comprising a flat flexible plate presenting a pair of opposite faces configured to be placed in contact with a wall of the uterus and an empty internal volume in fluidic connection with a vacuum pump. Each face comprises a plurality of holes such that when a negative pressure is created in the internal volume by the pump, the walls of the uterus are attracted by the respective face of the plate and held together, which mechanically shrinks the uterus, thereby compacting the muscles forming the wall of the uterus and constricting the blood vessels to stop bleeding. However, the size of the uterus may vary from one patient to another one. It may be difficult to introduce the hemostatic device in a little uterus like a partially retracted uterus. It may thus be necessary to provide different formats of the hemostatic device to allow the practitioner to select the one fitting best the patient's uterus. In addition, the size of the uterus also decreases as the uterus contracts. Thus, once the uterus has attained the size of the flexible plate, the hemostatic device may hinder further contraction of the uterus.

Document WO 2020/123525 teaches a hemostatic device for treating postpartum hemorrhage, comprising a flexible portion configured to be inserted into the uterus, a seal configured to close the opening of the uterus, and a vacuum pump in fluidic connection with holes provided in the flexible portion. When the uterus is sealed, the pump creates a negative pressure within the uterus via the holes in order to facilitate contractile movement of the uterine wall and vessel constriction. In this device, various means may be provided to protect the holes from occlusion by tissues. Because of the shape of this hemostatic device, when it is in a uterus, the area of the uterine wall which is in contact with the hemostatic device is limited. Consequently, the hemostatic effect of the contact between the hemostatic device and a bleeding area of the uterus is limited. Moreover, the space remaining between the uterine wall and the hemostatic device allows the vacuum to escape from the neck of the uterus. In order to reduce this depression, an inflatable balloon is required which makes the hemostatic device complicated to use. Furthermore, the pressure applied in the area of the neck of the uterus can be excessive as the area of the neck of uterus is fragile and not very extensible.

SUMMARY OF THE DISCLOSURE

There remains a need for a hemostatic device that can be easily inserted into a natural body cavity such as the uterus and conform to the shape of the cavity, while providing an efficient stimulation of the muscles forming the wall of the cavity and constriction of the blood vessels, without hindering further contraction of the uterus over time.

Some embodiments relate to a hemostatic device comprising:

- a hollow shaft extending from a first end to a second end, the shaft comprising an inner channel configured to be fluidically connected to a vacuum source,
- a plurality of hollow ribs, a first end of each rib being fixed to the first end of the shaft, each rib comprising an inner channel fluidically connected to the inner channel of the shaft and a plurality of holes leading to the inner channel of the respective rib,
- a membrane extending between the ribs and configured to be placed so as to face, at least partially, a bleeding area of a natural body cavity,
- the plurality of holes of each rib being arranged so as to face the bleeding area to induce a negative pressure in the natural body cavity when a negative pressure is applied by the vacuum source, the induced negative pressure being configured so that the wall of the natural cavity is attracted to the ribs, and
- a mechanism configured to move the ribs relative to the shaft between a retracted position allowing insertion and extraction of the hemostatic device into the natural cavity and an expanded position wherein the membrane and the ribs substantially fit the natural cavity.

According to advantageous and non-limiting features, taken alone or in any combination:

The membrane covers the ribs and comprises membrane holes placed so as to face the holes of the ribs.

The mechanism comprises a sliding assembly slidable along the shaft, the sliding assembly comprising a first sliding ring connected to a plurality of connecting rods, each connecting rod being connected to a respective rib, so that, when the first sliding ring is slid towards the first end of the shaft, the connecting rods make the ribs move to the expanded position.

The connecting rods are connected to the ribs by first pivot pins.

The connecting rods are connected to the first sliding ring by second pivot pins.

When the ribs are in the retracted position, the angle between the connecting rods and the shaft is lower than 45°.

The sliding assembly comprises a second sliding ring arranged to remain outside the natural cavity, the first sliding ring being closer to the first end of the shaft than the second sliding ring, the first sliding ring and the second sliding ring being rigidly connected so that the mechanism is operable by moving the second sliding ring.

The shaft comprises a first stop configured to stop the sliding of the sliding assembly towards the first end of the shaft.

The shaft comprises a second stop configured to reversibly stop the sliding of the sliding assembly towards the second end of the shaft when the ribs are in a maximum expanded position.

When the ribs are in a maximum expanded position, the angle between the connecting rods and the shaft is comprised between 90° and 100°.

The shaft comprises a third stop configured to reversibly stop the sliding of the sliding assembly towards the second end of the shaft when the ribs are in an intermediate expanded position and, when the ribs are in the intermediate maximum expanded position, the angle between the connecting rods and the shaft is higher than 45° and lower than 90°.

The holes in each rib are arranged in a constant pattern.

The hemostatic device comprises at least three ribs, the ribs being spaced from each other by a same angle.

The shaft is made of a rigid biocompatible polymer and the ribs are made of a flexible biocompatible polymer.

The membrane is made of a waterproof fabric or of an elastomer.

BRIEF DESCRIPTION OF THE FIGURES

Further features and advantages will be described in the following description, based on the appended drawings, in which.

Figure 1:
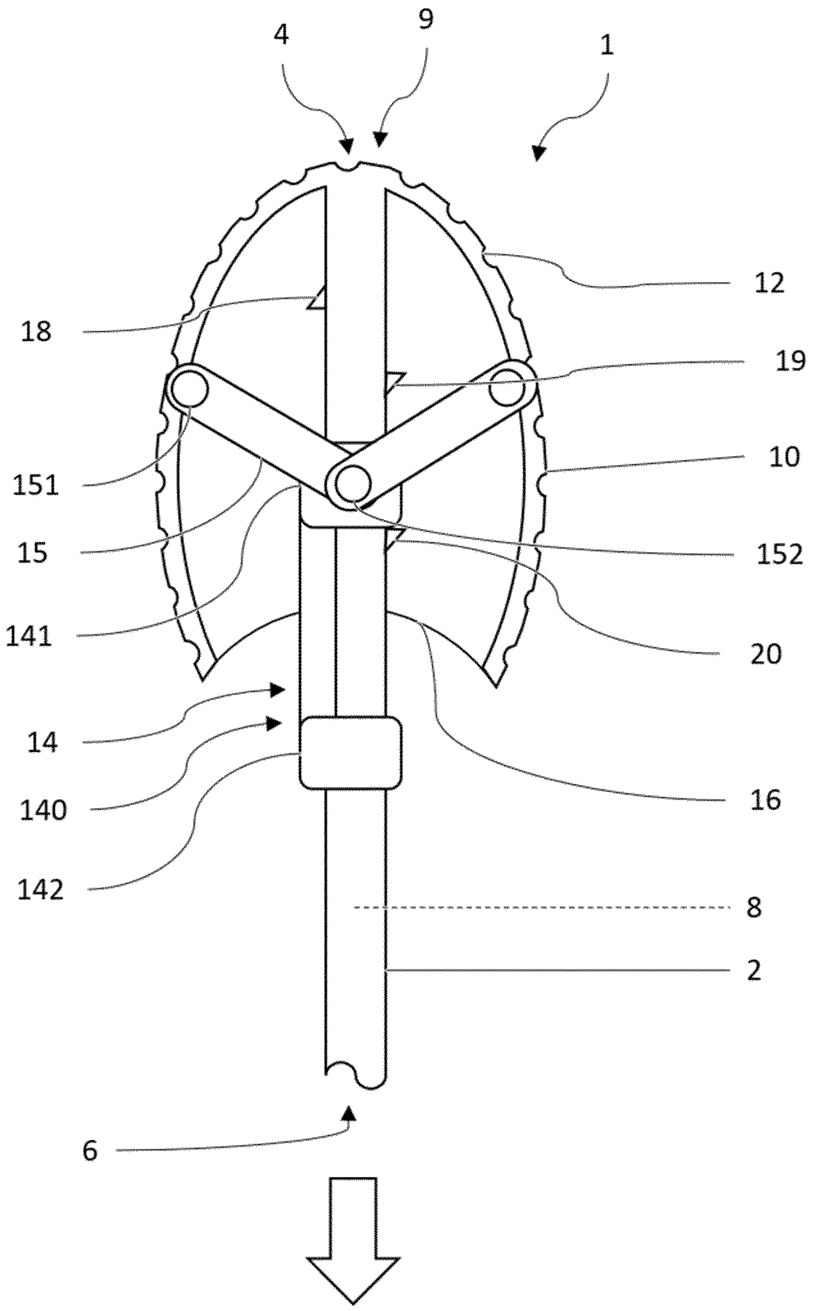
FIG. 1 is a side view of a hemostatic device.

For sake of legibility of the drawings, some components of the hemostatic device may have been omitted. In addition, the drawings are not necessarily drawn to scale.

In the drawings, identical reference signs designate elements that are identical to each other or that fulfil the same function. Thus, when one element has been described in detail with reference to one figure, it may not be described in detail again with reference to another figure.

DETAILED DESCRIPTION OF EMBODIMENTS

The invention relates to a hemostatic device configured to be inserted into a natural body cavity, such as a uterus, comprising a bleeding area.

The hemostatic device can have at least two positions comprising an expanded position and a retracted position.

The hemostatic device can be inserted into the natural body cavity in the retracted position; then it is expanded to substantially fit the natural body cavity. The wall of the natural body cavity is attracted to the hemostatic device due to the negative pressure induced in the natural body cavity by a vacuum circuit arranged in the hemostatic device, which causes bleeding to stop. The hemostatic device can be moved back to the retracted position to be extracted from the natural body cavity.

FIG. 1 illustrates a side view of a hemostatic device 1. The hemostatic device 1 comprises a hollow shaft 2 extending from a first end 4 to a second end 6. The hollow shaft 2 comprises an inner channel 8 configured to be fluidically connected to a vacuum source. To allow connecting the inner channel 8 of the shaft 2 to the vacuum source, the hemostatic device 1 advantageously comprises a base coupled to the second end 6 of the shaft 2 configured to connect to the vacuum source.

The hemostatic device 1 comprises a plurality of hollow ribs 10, a first end 9 of each rib 10 being fixed to the first end 4 of the shaft 2. The ribs 10 can be fixed to the shaft 2 in several possible ways. In some embodiments, the ribs 10 and the shaft 2 can be welded, tightly mounted, screwed or blocked by means of a third piece in the area of the first end 4 of the shaft 2 (like a nut system). In more preferred embodiments, the ribs 10 and the shaft 2 can be made in one single piece, for example by additive manufacturing, by injection manufacturing or by molding. Preferably, the shaft 2 and the ribs 10 are made of a flexible biocompatible polymer such as polyethylene (PE), polypropylene (PP), polyurethane (PU), polyethylene terephthalate (PET). In a preferred embodiment, the shaft 2 is more rigid than the ribs 10. Indeed, it is preferable that the hemostatic device 1 cannot bend too much so as to be easily inserted into a body cavity. However, the ribs 10 can be more flexible so as to be able to deform and fit the walls of a natural body cavity. Consequently, the ribs 10 can be made of a flexible biocompatible polymer which is even more flexible than the polymers already cited, such as thermoplastic elastomers (TPE) or thermoplastic polyurethane (TPU).

Typically, the hemostatic device 1 comprises between four and twelve ribs 10. Preferably, the hemostatic device 1 comprises at least three ribs 10 which are spaced from each other by a same angle. It can be understood here that the first ends 9 of the ribs 10 are fixed to the first end 4 of the shaft 2 in a constant pattern so that the angles between adjacent ribs 10 are equal. The hemostatic device 1 can be seen as having the shape of an umbrella and it is understood that each rib 10 is adjacent to two other ribs 10.

Figure 2:
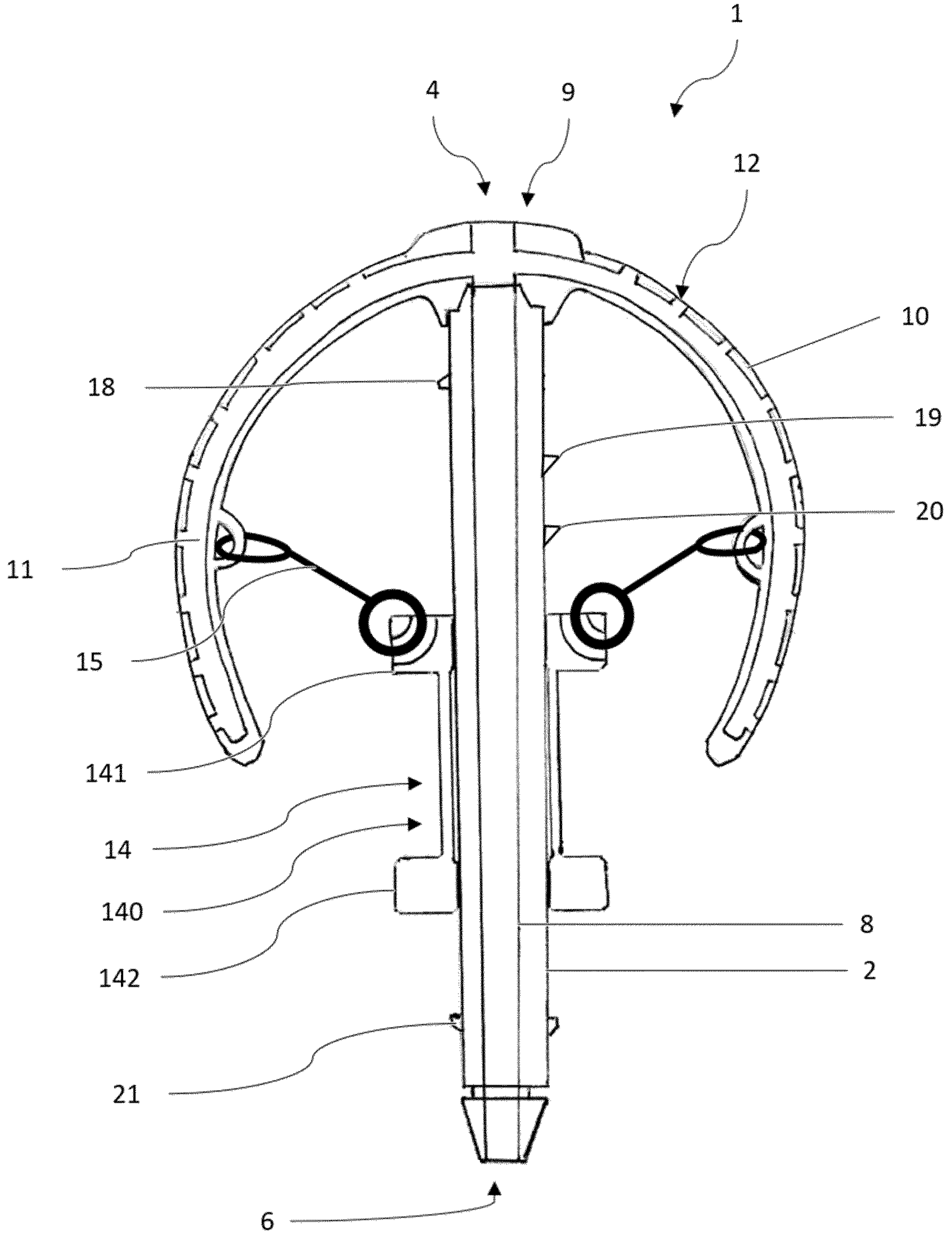
FIG. 2 is a sectional view of the hemostatic device.

FIG. 2 illustrates a sectional view of the hemostatic device 1. Each rib 10 comprises an inner channel 11 fluidically connected to the inner channel 8 of the shaft 2. Each rib 10 also comprises a plurality of holes 12. The plurality of holes 12 lead to the inner channel 11 of the respective rib 10. In other words, for each rib, the holes 12 lead to an inner channel 11 of a rib 10, the inner channel 11 of the rib 10 leading to the inner channel 8 of the shaft 2. It is understood that each rib 10 preferably comprises a plurality of holes 12. Thus, when vacuum is applied through the inner channel 8 of the hollow shaft 2, a negative pressure is created through the inner channels 11 of each rib 10 to the holes 12.

The plurality of holes 12 of each rib 10 are arranged so as to face the bleeding area to induce a negative pressure in the natural body cavity when a negative pressure is applied by the vacuum source, the induced negative pressure being configured so that the wall of the natural body cavity is attracted to the ribs 10.

Advantageously, the plurality of holes 12 in each rib 10 are arranged in a constant pattern. Preferably, in each rib 10, the holes 12 are equidistant. For example, the holes 12 can be regularly, in an equidistant manner, arranged along each rib 10. The distance between the holes 12 of the ribs 10 can range from 1 mm to 20 mm. Also, the diameter of the holes 12 of the ribs 10 ranges from 0.5 mm to 5 mm.

The hemostatic device 1 comprises a membrane 16 extending between the ribs 10 and configured to be placed so as to face, at least partially, a bleeding area of a natural body cavity. Preferably, the natural body cavity is a uterus.

In a first embodiment, the membrane 16 covers the ribs 10. In this embodiment, the membrane 16 is made of a single piece and does not comprise a plurality of pieces of membrane 160. Thus, the membrane 16 comprises membrane holes 13 facing the holes 12 of the ribs 10 so that the holes 12 of the ribs 10 are not sealed. Consequently, the vacuum can be applied into a body cavity via the holes 12. The diameter of the membrane holes 13 can be equal to the diameter of the holes 12 of the ribs 10. In another embodiment, the diameter of the membrane holes 13 can be greater than the diameter of the holes 12 of the ribs 10 so that it is easier to place the membrane 16 on the ribs 10 without the membrane 16 blocking the holes 12 of the ribs 10.

The membrane 16 can be fixed to the ribs 10 in several ways. For example, the membrane 16 can be stitched or welded to the ribs 10. The membrane 16 can also be fixed to the ribs 10 thanks to mechanical connections. For example, the ribs 10 can comprise notches thanks to which the membrane 16 is fixed to the ribs 10.

In a second embodiment, the membrane 16 can comprise a plurality of pieces of membrane 160, each piece of membrane 160 extending from a first rib 10 to a second rib 10 which is adjacent to the first rib 10. Each piece of membrane 160 thus extends between a respective pair of adjacent ribs 10.

The membrane 16 is preferably made of waterproof fabric or of an elastomer. For example, the membrane 16 can be made of woven or knitted textile with waterproof coating or can be an electrospun membrane with waterproof coating. In another example, the membrane 16 can be made by silicone molding or by thermoplastic elastomer (TPE) injection molding.

The thickness of the membrane 16 ranges preferably from 0.1 mm to 10 mm.

The hemostatic device 1 comprises a mechanism 14 configured to move the ribs 10 relative to the shaft 2. The mechanism 14 preferably comprises a sliding assembly 140 slidable along the shaft 2 and a plurality of connecting rods 15. The sliding assembly 140 comprises a first sliding ring 141 connected to the connecting rods 15, each connecting rod 15 being, on the opposite end, connected to a respective rib 10. Preferably, the connecting rods 15 are connected to the ribs 10 by first pivot pins 151. Also, preferably, the connecting rods 15 are connected to the first sliding ring 141 by second pivot pins 152.

Preferably, the sliding assembly 140 comprises a second sliding ring 142 arranged to remain outside the natural cavity when the hemostatic device 1 is in use. The second sliding ring 142 is further away from the first end 4 of the shaft 2 than the first sliding ring 141. In other words, the first sliding ring 141 is closer to the first end 4 of the shaft 2 than the second sliding ring 142. The first sliding ring 141 and the second sliding ring 142 are rigidly connected so that the mechanism 14 is operable by moving the second sliding ring 142. In a certain embodiment, the sliding assembly 140 can be made of one piece. The sliding assembly 140 is made of conventional polymers such as PE/PP/PET or polymers which are optimized to reduce friction, such as ePTFE (Expanded Polytetrafluoroethylene).

In a preferred embodiment, the shaft 2 comprises a first stop 18 configured to stop the sliding of the sliding assembly 140 towards the first end 4 of the shaft 2.

Figure 3:
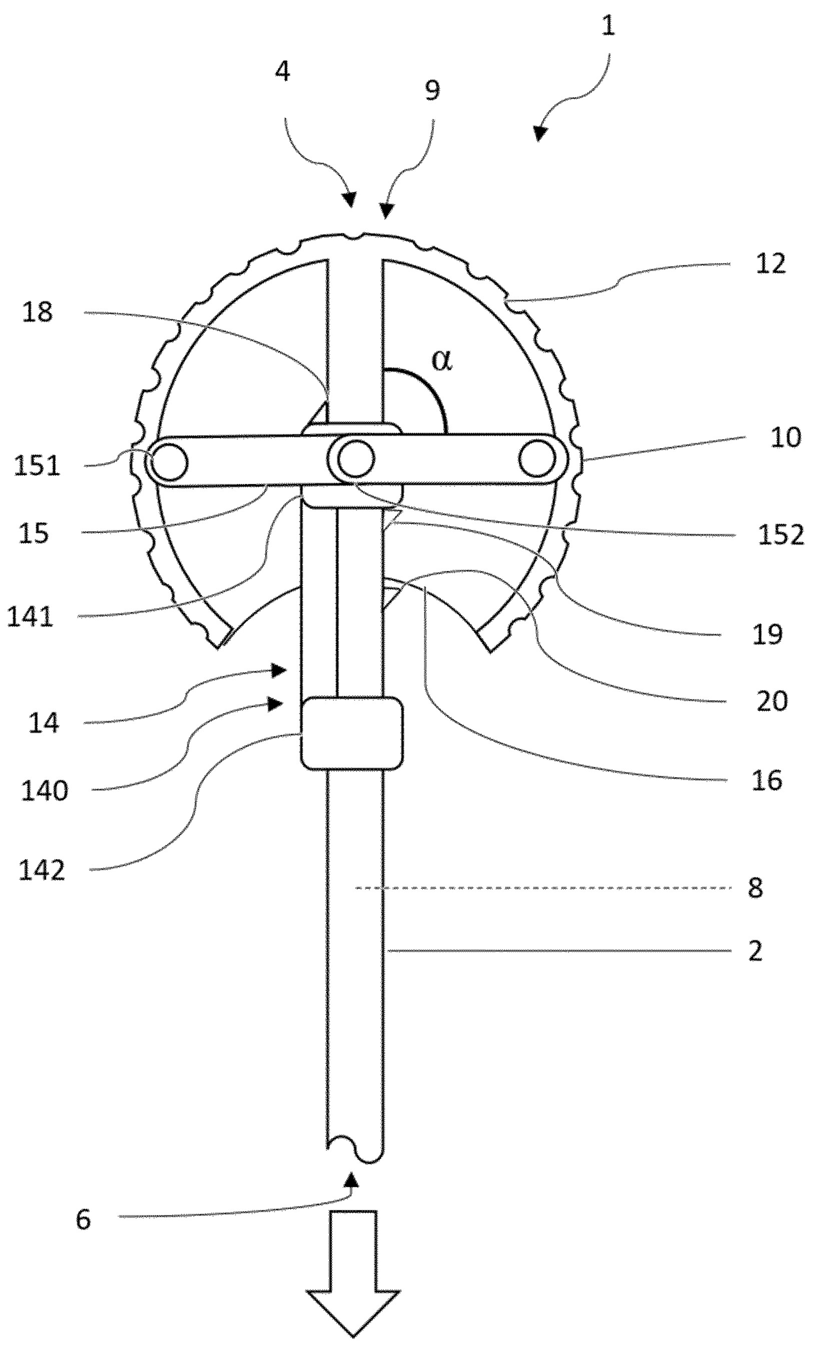
FIG. 3 is a side view of the hemostatic device when the ribs of the hemostatic device are in an expanded position.

Further, preferably, the hemostatic device comprises a second stop 19 configured to reversibly lock the ribs 10 in a maximum expanded position. In FIG. 3, the ribs of the hemostatic device illustrated are in an expanded position. To that end, the second stop prevents the sliding of the sliding assembly 140 towards the second end 6 of the shaft 2 once the ribs are in said maximum expanded position. For example, the second stop 19 may present an abutment surface extending radially from the shaft 2 and an inclined surface tapering from the abutment surface to the shaft. By “reversibly”, it is meant that the locking is temporary. As a result, the sliding assembly 140 is allowed to slide back to the second end 6 of the shaft 2 to bring the ribs to their retracted position if the second stop 19 is overcome which can be done in various ways. For example, the second stop 19 can be configured to enter in a slot made in the shaft 2 once a button is pressed or if a certain force is applied to the second stop 19.

In a certain embodiment, the hemostatic device 1 comprises a third stop 20 configured to reversibly lock the ribs 10 in an intermediate expanded position. It is understood that the third stop 20 is closer to the second end 6 of the shaft 2 than the second stop 19 is. The third stop 20 can be similar to the second stop 19.

In a certain embodiment, the hemostatic device 1 comprises a fourth stop 21 as illustrated in FIG. 2. The fourth stop 21 is configured to limit the movement of the sliding assembly 140 towards the second end 6. More particularly, the fourth stop 21 is configured to prevent the sliding assembly 140 to be taken apart from the shaft 2 when the sliding assembly 140 moves towards the second end 6.

Figure 4:
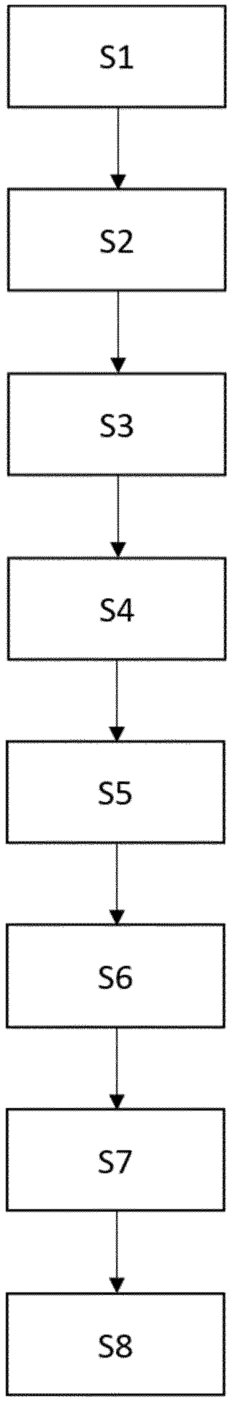
FIG. 4 schematically illustrates successive steps of operation of the hemostatic device.

A complete workflow of a treatment using the hemostatic device 1 will be described with reference to FIG. 4.

In step S1, the hemostatic device 1 is prepared by the medical staff. The preparation includes in particular unpacking the hemostatic device 1 from its package and connecting the inner channel 8 of the shaft 2 to the vacuum source.

In step S2, the hemostatic device 1 is inserted into the natural body cavity, for example the uterus. When the hemostatic device 1 is inserted into the natural body cavity, the ribs 10 are in a retracted position allowing the insertion of the hemostatic device 1 into the natural body cavity (and thus, obviously, allowing the extraction once that the bleeding has been stopped).

Figure 5:
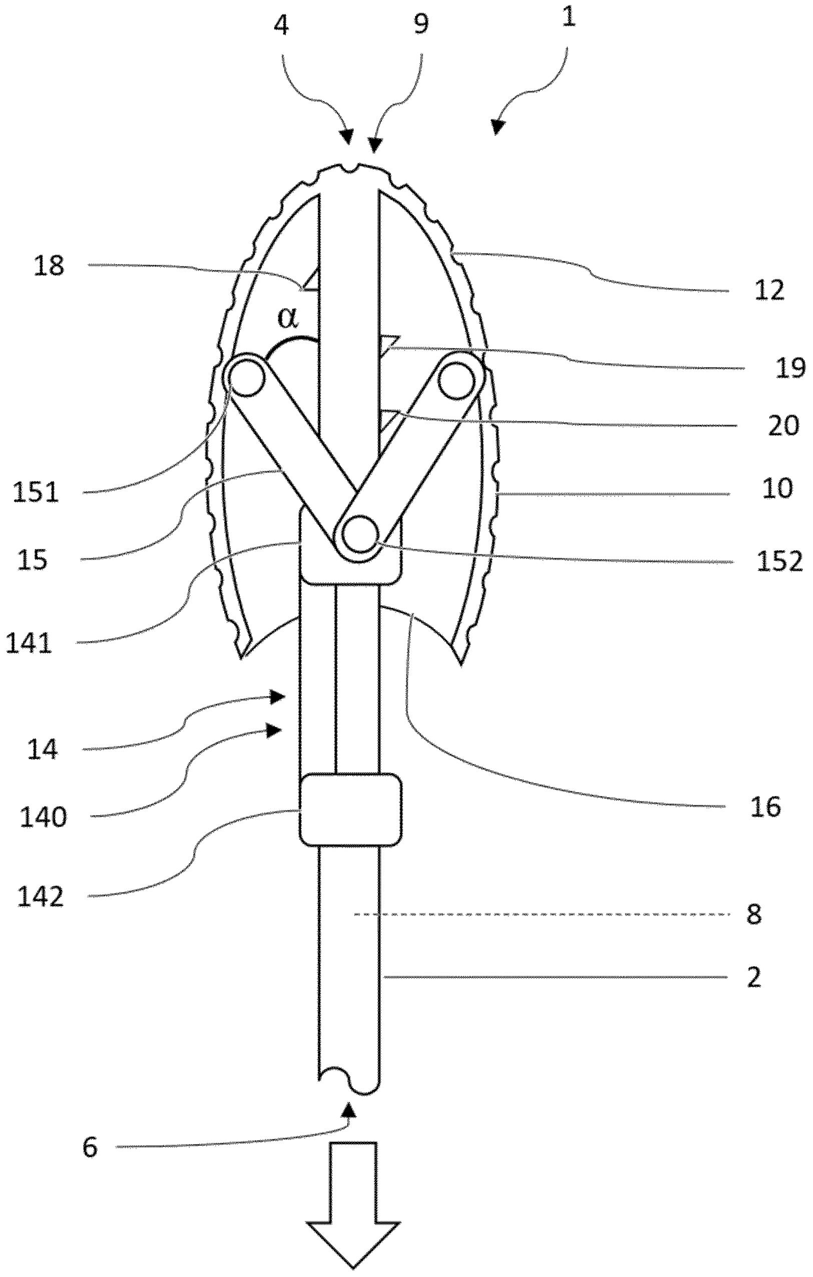
FIG. 5 is a side view of the hemostatic device when the ribs of the hemostatic device are in a retracted position.

More precisely, when the ribs 10 are in the retracted position, the angle between the connecting rods 15 and the shaft 2 is lower than 45°. FIG. 5 illustrates the hemostatic device 1 wherein the ribs 10 are in a retracted position. In FIG. 5, the angle between the connecting rods 15 and the shaft 2 is a.

In step S3, the sliding assembly 140 of the mechanism 14 is slid towards the first end 4 of the shaft 2 so that the mechanism 14 moves the ribs 10 relative to the shaft 2 towards an expanded position wherein the membrane 16 and the ribs 10 substantially fit the natural body cavity. By “fit the natural body cavity”, it is meant that the membrane 16 and the ribs 10 substantially fit the shape and the size of the natural body cavity. By “substantially fit”, it is meant that according to the size of the natural body cavity, the membrane 16 and the ribs 10 may not perfectly fit the internal wall of the natural body cavity, i.e. that the entire surfaces of the membrane 16 and of the ribs 10 may not be in contact with the internal wall of the natural body cavity. However, when the hemostatic device is in the expanded position and vacuum is applied though the holes of the ribs, the membrane and the ribs generally contact more than 50% of the surface of the natural body cavity, preferably more than 80% of the surface of the natural body cavity. Indeed, for example, the size and shape of the uterus may vary for every woman but providing that the membrane 16 and the ribs 10 substantially fit the natural body cavity allows maintaining the effectiveness of the hemostatic device regardless of such variations in size and shape. At the end of the step S3, the membrane 16 and the ribs 10 face, at least partially, a bleeding area of the natural body cavity.

More precisely, the second sliding ring 142 is slid by the medical staff towards the first end 4 of the shaft 2. Consequently, the sliding assembly 140, i.e. the first sliding ring 141, the second sliding ring 142 and the rigid connection between the rings, is slid. Hence, the connecting rods 15 move and make the ribs 10 move to the expanded position.

Generally, the sliding assembly 140 is slid to the first stop 18 so that the ribs 10 are in the maximum expanded position. Preferably, when the ribs 10 are in the maximum expanded position, the angle between the connecting rods 15 and the shaft 2 is comprised between 90° and 100°. In other terms, as illustrated in FIG. 3, the angle α is greater than or equal to 90°. Preferably, the maximum expanded position corresponds to a position wherein the ribs 10 and, thus, the membrane 16, fit the wall of the natural body cavity. Further, the sliding of the sliding assembly 140 is stopped by the second stop 19 so that it is not necessary for the medical staff to maintain the second sliding ring 142 in a certain position.

In a certain embodiment, the hemostatic device 1 is adapted to several types of natural body cavities. For example, one same hemostatic device 1 can be adapted to a uterus and to a bladder. Thus, the hemostatic device 1 can be adapted to natural body cavities which do not have the same size. Consequently, in this case, the sliding assembly 140 can be slid until the ribs are in an intermediate expanded position. Thus, the sliding assembly 140 is slid until the first sliding ring 141 has overtaken the third stop 20. When the ribs 10 are in the intermediate expanded position, the angle between the connecting rods 15 and the shaft 2 is higher than 45° and lower than 90°. FIG. 1 shows the hemostatic device 1 when the ribs 10 are in an intermediate expanded position.

Thanks to the second stop 19 or the third stop 20, the sliding assembly 140 is stopped so that it is not necessary for the medical staff to maintain the second sliding ring 142 in a certain position. It is understood here that the second stop 19 and the third stop 20 have the same role but the second stop 19 is configured to stop the sliding of the sliding assembly 140 when the sliding assembly 140 is closer to the first end 4 of the shaft 2 than the sliding assembly 140 when it is stopped by the third stop 20. The third stop 20 can also be seen as a safety in the case the second stop 19 is deficient.

Figure 6:
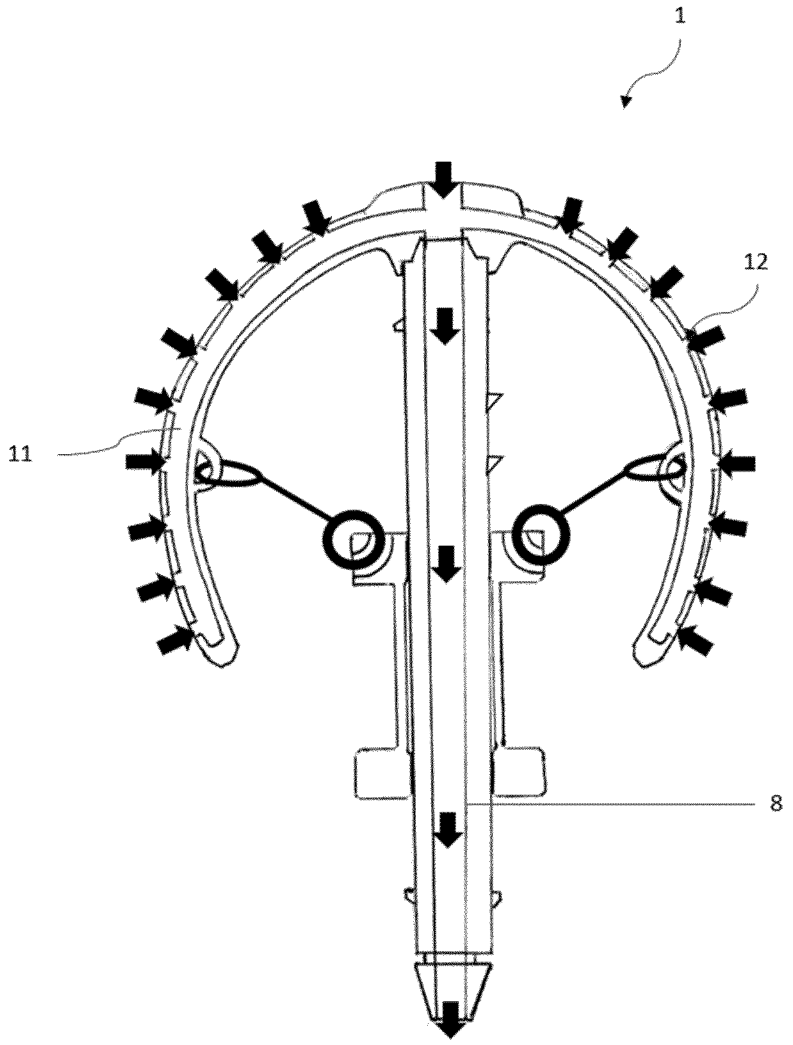
FIG. 6 schematically illustrates the circulation of the vacuum into the hemostatic device.

In step S4, the vacuum source is turned on so that a depression is applied into the natural body cavity. Indeed, it is reminded that the inner channel 8 of the shaft 2 is fluidically connected to the inner channels 11 of the ribs 10, the inner channels 11 of the ribs 10 being fluidically connected to the natural body cavity through the holes 12 of the ribs 10. FIG. 6 schematically illustrates the circulation of the vacuum into the hemostatic device 1. As a result, the wall of the natural body cavity is attracted by the ribs 10.

The level of vacuum applied, i.e. the negative pressure applied in the natural body cavity, depends on the clinical case. In the case of a uterus, if the uterus is capable of contracting again quite autonomously, it only needs to be incited to contract again and a low negative pressure is sufficient, for example a negative pressure of 10 mbar. However, if the uterus is lifeless, an important negative pressure is necessary, for example a negative pressure of 1000 mbar.

Step S5 is a first stabilization step, in which the vacuum is maintained. Hemostasis is initiated by a dual action of the hemostatic device: (1) direct contact between the wall of the natural body cavity and the ribs 10 and the membrane 16 of the hemostatic device 1 (promoting a so-called "contact hemostasis") and (2) compression of the wall of the natural body cavity and its internal structure by aspiration. Thanks to the fact that the holes 12 of the ribs are arranged in a constant pattern, the vacuum distribution is homogeneous.

In step S6, the medical staff slides the second sliding ring 142 toward the second end 6 of the shaft 2 so that the sliding assembly 140 slides towards the second end 6 of the shaft 2. Consequently, the ribs 10 of the hemostatic device 1 are gradually retracted. Firstly, the sliding assembly 140 can be slid until the third stop 20 so that the ribs 10 are in the intermediate position. Then, the sliding assembly 140 can be slid until the ribs 10 reach the retracted position. Thus, the third stop 20 allows to retract the ribs 10 gradually. At the end of said step (see FIG. 5), the ribs 1 are in the retracted position. During said step, the natural body cavity size decreases, and a negative pressure may be maintained by the vacuum source. The reduction of the size of the natural body cavity promotes the contraction of the muscles. These contractions compress the vessels and stop the bleeding permanently.

Step 6 is performed manually by the medical staff. It is reminded that, before step 6, the sliding assembly 140 is normally stopped by the second stop 19 or the third stop 20. In order to free the sliding assembly 140, the medical staff can pull the sliding assembly 140 towards the second end 6 of the shaft and applying a force higher enough to make the sliding assembly 140 overtake the second stop 19 or the third stop 20. In another embodiment, the medical staff can press a button which make the stops 19, 20 deactivated. The man skilled in the art knows types of stops described and methods to use them.

In a possible embodiment, step 6 can be triggered by the natural body cavity itself. Indeed, if the uterus contracts again, the wall of the uterus applies a force on the ribs 10 of the hemostatic device 1. The force can be strong enough to make the sliding assembly 140 overtake the second stop 19 or the third stop 20 without any manual intervention.

In step S7, the negative pressure is stopped, i.e. the vacuum source is turned off.

In step S8, the hemostatic device 1 is extracted from the natural body cavity, and the medical procedure ends, after a minimal treatment time of 10 minutes for example, depending on the specific protocol.

The invention claimed is:

1. A hemostatic device comprising:

a hollow shaft extending from a first end to a second end, the hollow shaft comprising an inner channel of the hollow shaft configured to be fluidically connected to a vacuum source;

a plurality of hollow ribs, a first end of each hollow rib being fixed to the first end of the hollow shaft, each hollow rib comprising an inner channel of a respective hollow rib fluidically connected to the inner channel of the hollow shaft and a plurality of holes leading to the inner channel of the respective hollow rib;

a membrane extending between the hollow ribs and configured to be placed so as to face, at least partially, a bleeding area of a natural body cavity, the plurality of holes of each hollow rib being arranged so as to face the bleeding area to induce a negative pressure in the natural body cavity when a negative pressure is applied by the vacuum source, the induced negative pressure being configured so that the wall of the natural cavity is attracted to the hollow ribs; and a mechanism configured to move the hollow ribs relative to the hollow shaft between a retracted position allowing insertion and extraction of the hemostatic device into the natural cavity and an expanded position wherein the membrane and the hollow ribs substantially fit the natural cavity, wherein the mechanism comprises a sliding assembly slidable along the hollow shaft, the sliding assembly comprising a first sliding ring connected to a plurality of connecting rods, each connecting rod being connected to a respective hollow rib, so that, when the first sliding ring is slid towards the first end of the hollow shaft, the connecting rods make the hollow ribs move to the expanded position.

2. The hemostatic device according to claim 1, wherein the membrane covers the hollow ribs and comprises membrane holes placed so as to face the holes of the hollow ribs.

3. The hemostatic device according to claim 1, wherein the connecting rods are connected to the hollow ribs by first pivot pins.

4. The hemostatic device according to claim 1, wherein the connecting rods are connected to the first sliding ring by second pivot pins.

5. The hemostatic device according to claim 1, wherein, when the hollow ribs are in the retracted position, an angle between the connecting rods and the hollow shaft is lower than 45°.

6. The hemostatic device according to claim 1, wherein the sliding assembly comprises a second sliding ring arranged to remain outside the natural cavity, the first sliding ring being closer to the first end of the hollow shaft than the second sliding ring, the first sliding ring and the second sliding ring being rigidly connected so that the mechanism is operable by moving the second sliding ring.

7. The hemostatic device according to claim 1, wherein the hollow shaft comprises a first stop configured to stop a sliding of the sliding assembly towards the first end of the hollow shaft.

8. The hemostatic device according to claim 1, wherein the hollow shaft comprises a second stop configured to reversibly stop a sliding of the sliding assembly towards the second end of the hollow shaft when the hollow ribs are in a maximum expanded position.

9. The hemostatic device according to claim 8, wherein when the hollow ribs are in a maximum expanded position, an angle between the connecting rods and the hollow shaft is comprised between 90° and 100°.

10. The hemostatic device according to claim 1, wherein the hollow shaft comprises a third stop configured to reversibly stop the sliding of the sliding assembly towards the second end of the hollow shaft when the hollow ribs are in an intermediate expanded position and, when the hollow ribs are in the intermediate maximum expanded position, an angle between the connecting rods and the hollow shaft is higher than 45° and lower than 90°.

11. The hemostatic device according to claim 1, wherein the holes in each hollow rib are arranged in a constant pattern.

12. The hemostatic device according to claim 1, comprising at least three hollow ribs, the hollow ribs being spaced from each other by a same angle.

13. The hemostatic device according to claim 1, wherein the hollow shaft is made of a rigid biocompatible polymer and the hollow ribs are made of a flexible biocompatible polymer.

14. The hemostatic device according to claim 1, wherein the membrane is made of a waterproof fabric or of an elastomer.

15. The hemostatic device according to claim 1, wherein the membrane comprises a plurality of pieces of membrane, each piece of membrane extending from a first rib of the plurality of hollow ribs to a second rib of the plurality of hollow ribs, between the first rib and the second rib, the second rib being adjacent to the first rib.

* * * * *